(12) United States Patent
Blanchard

(10) Patent No.: US 10,893,887 B2
(45) Date of Patent: Jan. 19, 2021

(54) INTRAOSSEOUS ACCESS DEVICE

(71) Applicant: C. R. Bard, Inc., Franklin Lakes, NJ (US)

(72) Inventor: Daniel B. Blanchard, Bountiful, UT (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 262 days.

(21) Appl. No.: 15/796,471

(22) Filed: Oct. 27, 2017

(65) Prior Publication Data

US 2018/0116693 A1 May 3, 2018

Related U.S. Application Data

(60) Provisional application No. 62/413,879, filed on Oct. 27, 2016.

(51) Int. Cl.
*A61B 17/34* (2006.01)
*A61M 39/02* (2006.01)
(Continued)

(52) U.S. Cl.
CPC ...... *A61B 17/3472* (2013.01); *A61B 17/3415* (2013.01); *A61B 17/3423* (2013.01);
(Continued)

(58) Field of Classification Search
CPC ............ A61B 17/3472; A61B 17/3415; A61B 17/3496; A61B 17/3494; A61B 17/3423;
(Continued)

(56) References Cited

U.S. PATENT DOCUMENTS

| 5,040,542 A | 8/1991 | Gray |
| 5,042,558 A | 8/1991 | Hussey et al. |

(Continued)

FOREIGN PATENT DOCUMENTS

| EP | 0232600 A1 | 8/1987 |
| EP | 0548612 A1 | 6/1993 |

(Continued)

OTHER PUBLICATIONS

PCT/US2017/058863 filed Oct. 27, 2017 International Search Report and Written Opinion dated Jan. 29, 2018.
(Continued)

*Primary Examiner* — Brandy S Lee
*Assistant Examiner* — Nidah M Hussain
(74) *Attorney, Agent, or Firm* — Rutan & Tucker LLP

(57) ABSTRACT

An access device configured for inserting an intraosseous catheter into an interior portion of a bone is disclosed. In one embodiment, an intraosseous access device is disclosed, comprising a device body, a trocar needle included with the device body, and an intraosseous catheter removably disposed on the trocar needle. The device body is configured to enable a user of the access device to manually insert a distal tip of the trocar needle through a skin surface of a body of a patient to an external surface of a bone of the patient. An advancement mechanism is also disclosed and is configured to selectively and distally advance the trocar needle and intraosseous catheter a predetermined distance into an internal portion of the bone of the patient after the distal tip of the trocar needle has been inserted to the external surface of the bone.

19 Claims, 10 Drawing Sheets

(51) Int. Cl.
  *A61M 5/158* (2006.01)
  *A61M 25/06* (2006.01)
  *A61M 39/10* (2006.01)
(52) U.S. Cl.
  CPC ...... *A61B 17/3494* (2013.01); *A61B 17/3496* (2013.01); *A61M 5/158* (2013.01); *A61M 25/065* (2013.01); *A61M 39/0247* (2013.01); *A61M 39/10* (2013.01); *A61M 2039/025* (2013.01); *A61M 2039/0273* (2013.01); *A61M 2039/0291* (2013.01)
(58) Field of Classification Search
  CPC ............... A61M 5/158; A61M 25/065; A61M 39/0247; A61M 39/10; A61M 2039/025; A61M 2039/0291; A61M 2039/0273
  USPC ........................................................ 604/513
  See application file for complete search history.

(56) References Cited

U.S. PATENT DOCUMENTS

| | | | |
|---|---|---|---|
| 5,591,188 A | 1/1997 | Waisman | |
| 5,601,559 A | 2/1997 | Melker et al. | |
| 5,746,720 A * | 5/1998 | Stouder, Jr. | A61B 17/3417 604/117 |
| 5,807,275 A | 9/1998 | Jamshidi | |
| 2004/0220497 A1 | 11/2004 | Findlay et al. | |
| 2005/0033235 A1 | 2/2005 | Flint | |
| 2005/0165403 A1* | 7/2005 | Miller | A61B 17/32053 606/79 |
| 2009/0204024 A1 | 8/2009 | Miller | |
| 2009/0306697 A1 | 12/2009 | Fischvogt | |
| 2010/0280410 A1* | 11/2010 | Moos | A61B 10/025 600/567 |
| 2010/0312246 A1* | 12/2010 | Browne | A61B 17/1615 606/87 |
| 2014/0046327 A1 | 2/2014 | Tzachar et al. | |
| 2014/0276366 A1 | 9/2014 | Bourne et al. | |
| 2015/0127006 A1 | 5/2015 | Miller | |

FOREIGN PATENT DOCUMENTS

| | | |
|---|---|---|
| WO | 2005/046769 A2 | 5/2005 |
| WO | 2015/177612 A1 | 11/2015 |
| WO | 2019/051343 A1 | 3/2019 |

OTHER PUBLICATIONS

EP 17864208.8 filed May 24, 2019 Extended European Search Report filed May 19, 2020.

* cited by examiner

INTRAOSSEOUS ACCESS DEVICE

CROSS-REFERENCE TO RELATED APPLICATIONS

This application claims the benefit of U.S. Provisional Patent Application No. 62/413,879, filed Oct. 27, 2016, and entitled "Intraosseous Access Device," which is incorporated herein by reference in its entirety.

BRIEF SUMMARY

Briefly summarized, present embodiments are directed to an access device configured for inserting an intraosseous catheter into an interior portion of a bone. Such access is desired in certain situations to enable rapid infusion of medicaments into the interior intraosseous portion of the bone, which medicaments can then be quickly assimilated into the body. In accordance with embodiments to be described, the access devices disclosed herein are capable of inserting the intraosseous catheter a predetermined distance into the bone interior, which enables the user of the device to accurately place the distal tip of the catheter where desired within the intraosseous region, in contrast to known intraosseous devices.

In one embodiment, an intraosseous access device is disclosed, comprising a device body, a trocar needle included with the device body, and an intraosseous catheter removably disposed on the trocar needle. The device body is configured to enable a user of the access device to manually insert a distal tip of the trocar needle through a skin surface of a body of a patient to an external surface of a bone of the patient. An advancement mechanism is also disclosed and is configured to selectively and distally advance the trocar needle and intraosseous catheter into an internal portion of the bone of the patient after the distal tip of the trocar needle has been inserted to the external surface of the bone.

In addition to the above, other access device and intraosseous catheter configurations are disclosed.

These and other features of embodiments of the present invention will become more fully apparent from the following description and appended claims, or may be learned by the practice of embodiments of the invention as set forth hereinafter.

BRIEF DESCRIPTION OF THE DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DETAILED DESCRIPTION OF SELECTED EMBODIMENTS

Reference will now be made to figures wherein like structures will be provided with like reference designations. It is understood that the drawings are diagrammatic and schematic representations of exemplary embodiments of the present disclosure, and are neither limiting nor necessarily drawn to scale.

For clarity it is to be understood that the word "proximal" refers to a direction relatively closer to a clinician using the device to be described herein, while the word "distal" refers to a direction relatively further from the clinician. For example, the end of a catheter placed within the body of a patient is considered a distal end of the catheter, while the catheter end remaining outside the body is a proximal end of the catheter. Also, the words "including." "has," and "having," as used herein, including the claims, shall have the same meaning as the word "comprising."

Embodiments of the present disclosure are generally directed to an access device configured for inserting an intraosseous catheter into an interior portion of a bone. Such access is desired in certain situations to enable rapid infusion of medicaments into the interior intraosseous portion of the bone, which medicaments can then be quickly assimilated into the body. In accordance with embodiments to be described, the access devices disclosed herein are capable of inserting the intraosseous catheter a predetermined distance into the bone interior, which enables the user of the device to accurately place the distal tip of the catheter where desired within the intraosseous region, in contrast to known intraosseous devices.

Figure 1:
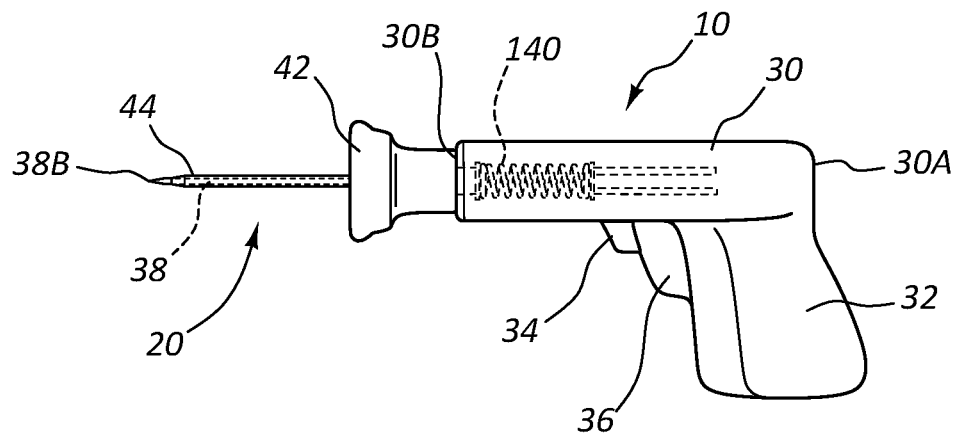
FIG. 1 is a side view of an intraosseous access device according to one embodiment.

FIG. 1 depicts various details of an intraosseous access device ("access device"), generally designated at 10, according to one embodiment. The access device 10 is shown with an intraosseous catheter ("catheter") 20, also referred to as an intraosseous cannula, removably included therewith. Though further details will be given below, in the present embodiment the catheter 20 generally includes a hub 42 and an attached cannula 44 that extends between a proximal end 44A and a distal end 44B. The cannula 44 is slidably received over a trocar needle ("trocar") 38 that distally extends from the access device 10 and terminates at a distal tip 38B.

As shown, the access device 10 includes a body 30 extending between a proximal end 30A and a distal end 30B. In the present embodiment, the body 30 is shaped to define a pistol grip suitable for grasping by a user of the access device 10, though many other suitable shapes for the body are possible.

The body 30 houses an advancement mechanism configured to selectively advance the trocar 38 and catheter 20 included therewith in a distal direction during use of the access device 10. In the present embodiment, the advancement mechanism includes an internal spring that is mounted within the body 30 and operably connected to the trocar 38. The spring is selectively releasable by an actuator, such as a release trigger 36, as to advance the trocar 38 distally with respect to the body 30. This enables the trocar 38 and the catheter 20 included therewith to be driven into a bone of the patient, as will be described further below. As illustrated in FIG. 1, a safety switch 34 is also included and configured to prevent inadvertent actuation of the release trigger 36 by the user. In the present embodiment, the safety switch 34 is positioned adjacent the release trigger 36 and must be displaced from its original position, such as by sliding, so as to enable the release trigger to be actuated by a finger of the user, for instance. Of course, other safety switch and release trigger configurations can be employed.

Figure 2A:
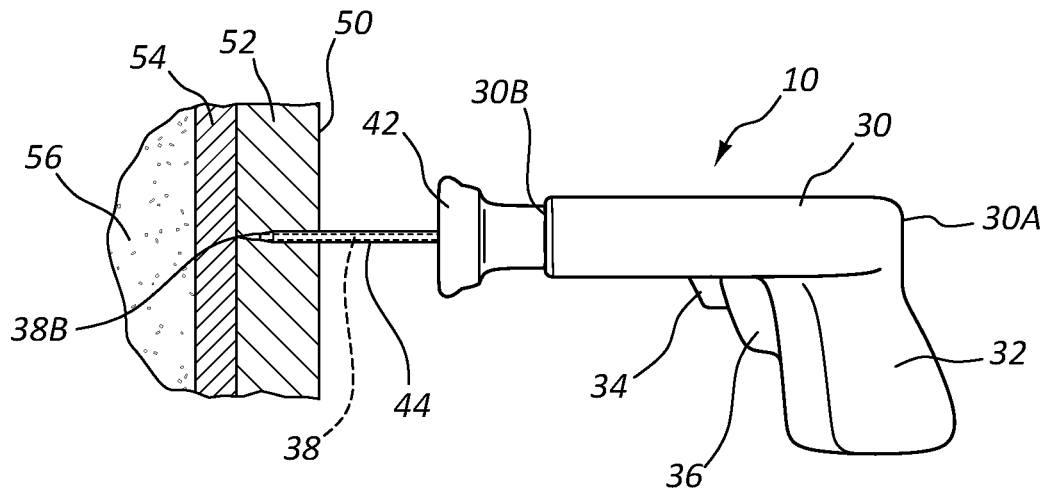
FIGS. 2A-2D depict various stages of use of an access device such as that shown in FIG. 1.
Figure 2B:
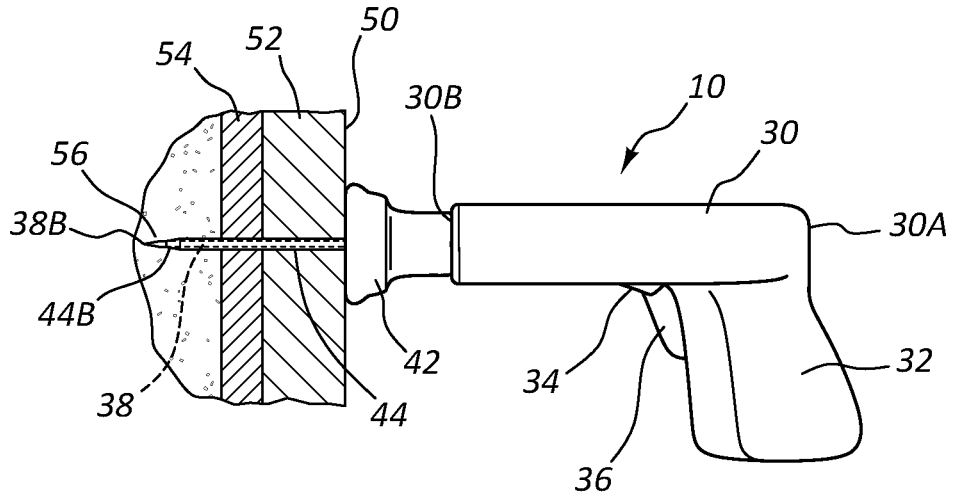

FIGS. 2A-2D depict various stages of use of the access device 10 in inserting the catheter 20 into a bone of a patient, according to one embodiment. For clarity, the hand of the user is omitted from the figures. As shown in FIG. 2A, the user grasps the body 30 of the access device and directs the distal tip 38B of the trocar 38 via manual force through a skin surface 50 and subcutaneous tissue 52 of the patient until the distal tip of the trocar impacts a wall ("bone wall") 54 of the bone. At this point, the safety switch 34 is disengaged by the user and the release trigger 36 is depressed by a finger of the user, which in turn causes the internal spring (or other suitable advancement mechanism) to distally drive the trocar distal tip 38B through the bone wall 54 and into the interior, bone marrow 56, of the bone, as seen in FIG. 2B. This also places the distal tip 44B of the catheter cannula 44 in the bone marrow 56, as desired. Note that the internal spring, as an advancement mechanism, serves as one example of a selective means for advancing the trocar and the catheter. It is appreciated that other structures and components can be employed to provide the same functionality, in other embodiments, including a drill, a chemical or other charges, controlled explosive charges, etc.

Note that the access device 10 and the advancement mechanism are configured to advance the cannula distal tip 44B a predetermined distance into the bone. In one embodiment, the predetermined distance can vary from about 0.25 inch to about 1 inch into the bone, though a variety of other possible depths are possible. The variation in predetermined depth may be needed in accessing bones of differing thicknesses. In one embodiment, a depth selector, such as a depth dial, can be included on the access device body 30. With such a depth dial, the user can select the desired depth that the advancement mechanism will advance the distal tip 44B of the cannula 44. The depth dial in such an embodiment can vary the pre-actuation compression of the spring so as to achieve a corresponding advancement of the trocar 38 and catheter 20 according to the depth dial setting. In other embodiments, other controls can be employed to vary actuation of the spring or other advancement mechanism according to predetermined desired depths. In yet another embodiment, the access device 10 can be configured to insert the trocar 38 and catheter 20 to one, pre-set depth.

Figure 2C:
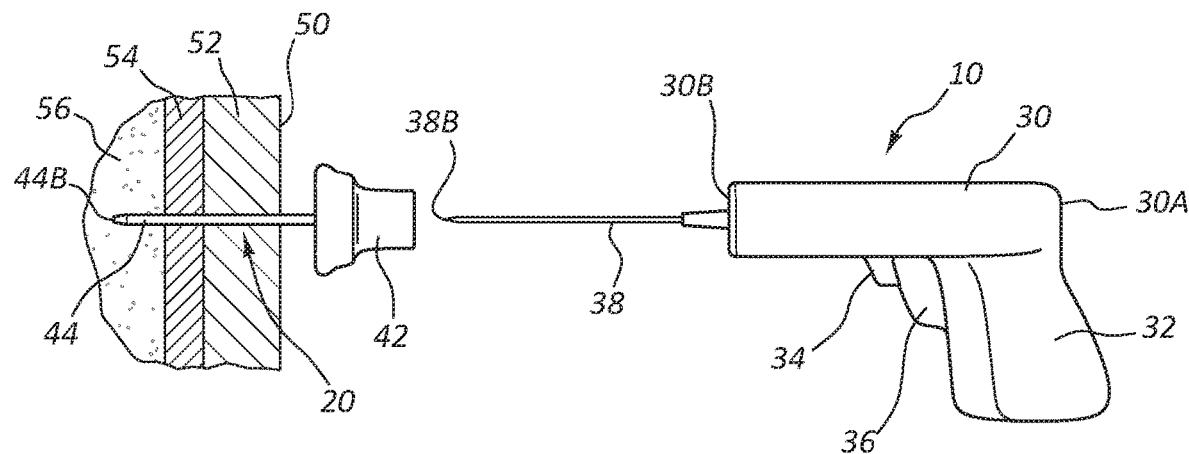
Figure 2D:
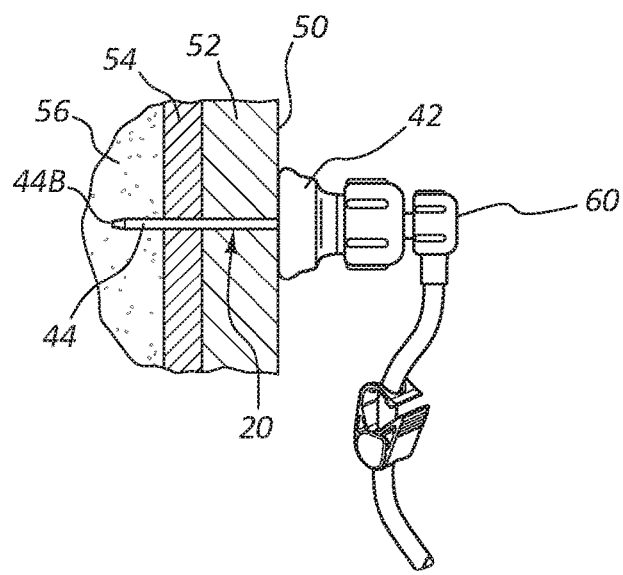

In FIG. 2C, the trocar 38 is withdrawn from the cannula 44 of the catheter 20 by proximally withdrawing the access device body 30, thus causing separation of the access device 10 from the catheter 20. After withdrawal of the access device 10, the cannula 44 remains in place with its distal tip 44B disposed within the bone marrow 56, as shown. Note that the catheter hub 42 is spaced apart from the skin surface 50 at this point. In FIG. 2D, the catheter 20 is adjusted such that the hub 42 is adjacent the skin surface 50, as explained in further detail below. Also, an extension set 60 is shown operably attached to the hub 42 so as to enable medicaments or other fluids to be infused through the catheter 20 and into the bone marrow 56 via the catheter cannula 44.

Figure 3A:
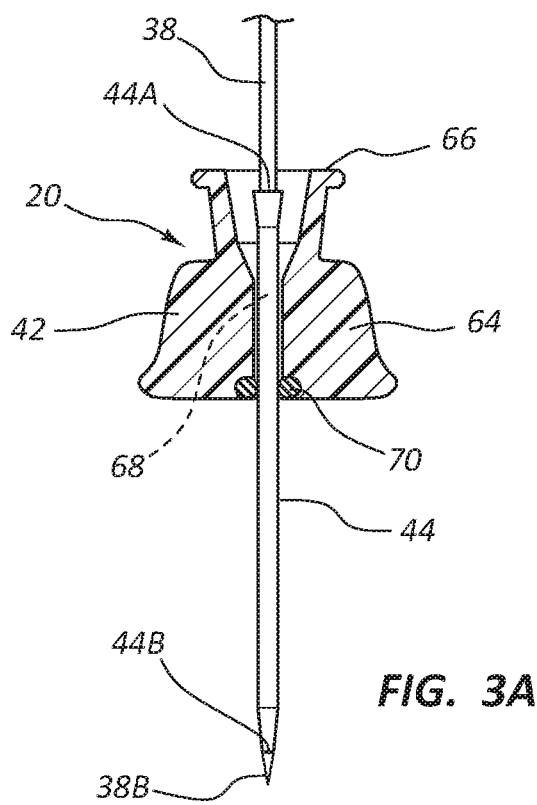
FIGS. 3A-3D depict various views of an intraosseous catheter according to one embodiment.
Figure 3B:
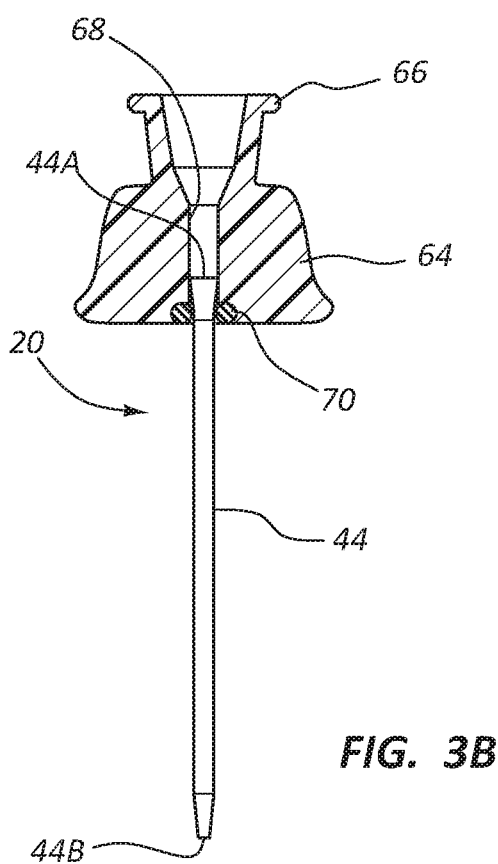
Figure 3C:
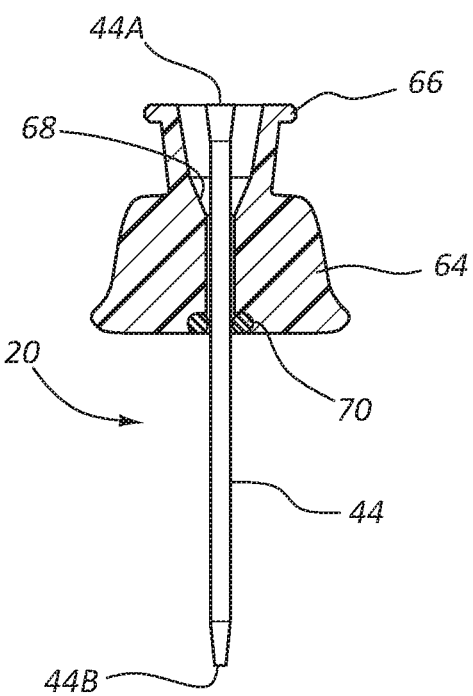

FIGS. 3A-3D depict various details of the catheter 20 according to one embodiment, wherein the hub 42 defines a base portion 64 and a connector portion 66 configured to enable the extension set 60 to operably connect with the catheter. The hub 42 includes a lumen 68 that cooperates with the cannula 44 to define a fluid path to allow the passage of fluids through the catheter. As shown, the cannula 44—which in this embodiment includes a sufficiently rigid material such as stainless steel, PEEK, or other suitable metals/thermoplastics/materials—is slidable with respect to the hub 42 so as to enable the total length of the catheter 20 to be adjusted—a relatively long length for a deep cannula distal tip placement as shown in FIG. 3B, and a relatively short length for a shallow cannula distal tip placement as shown in FIG. 3C. This in turn enables the hub 42 of the catheter 20 to rest against the skin surface 50, as shown in FIG. 2D, regardless of the depth of the distal tip 44B of the cannula 44. If not adjustable, the catheter may present a situation where the hub 42 is spaced apart from the skin surface 50, similar to what is shown in FIG. 2C.

Figure 3D:
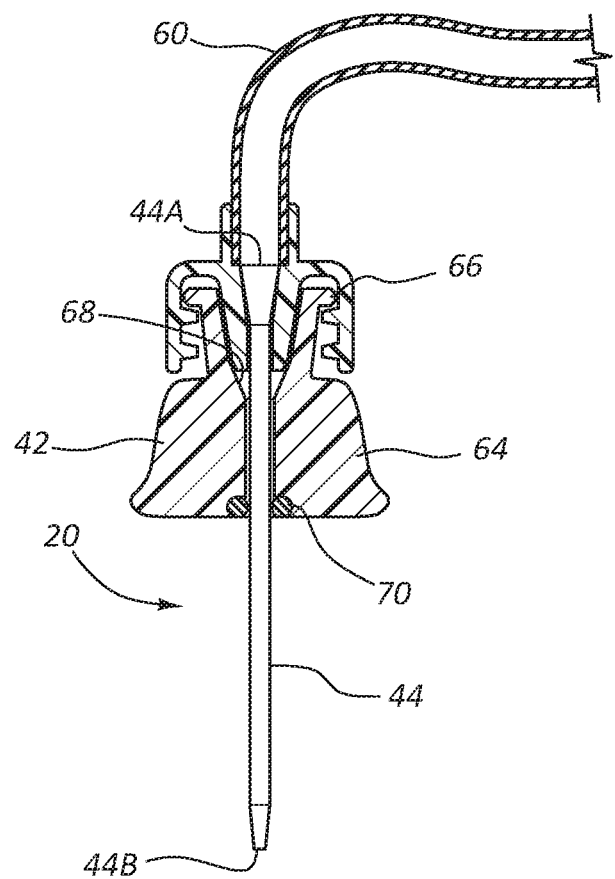

In greater detail, the variation in extension of the cannula 44 from the hub 42 is made possible by an O-ring 70 that is interposed within the lumen 68 between the base portion 64 of the hub 42 and an outer surface of the cannula 44, which in turn enables the cannula to longitudinally slide within the hub lumen in a fluid-tight arrangement. It is appreciated that the O-ring 70 can be located in other positions within the lumen 68 of the hub 42 and that other fluid sealing modes in addition to an O-ring can be utilized. FIG. 3D, shows that, in the present embodiment, the cannula 44 can be withdrawn into the hub 42 such that it extends past the connector portion 66 of the hub and into the extension set 60, thus enabling further shortening of the overall longitudinal length of the catheter 20.

Figure 4:
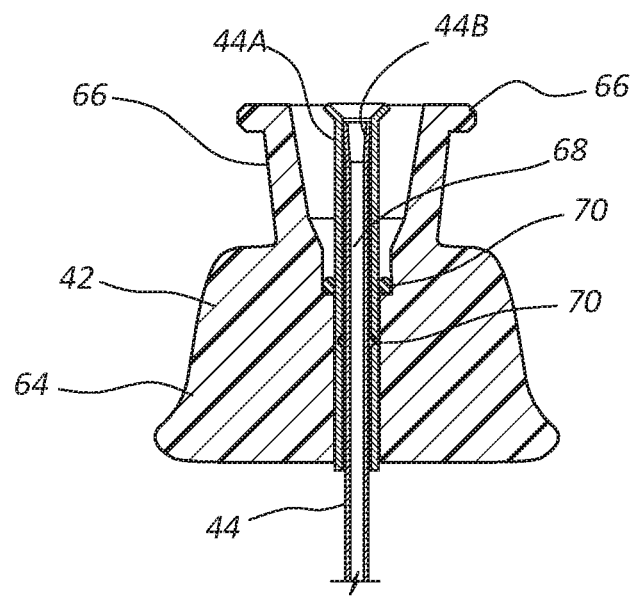
FIG. 4 is a cross-sectional side view of an intraosseous catheter according to one embodiment.

FIG. 4 depicts the catheter 20 according to another embodiment, wherein the cannula 44 includes a first cannula portion 44A and a second cannula portion 44B that are telescopically mated to one another with two O-rings 70 interposed therebetween and between the first cannula portion and the lumen 68 of the hub base portion 64 as to enable the cannula portions to extend and contract relative to one another and the hub base portion. Such a telescoping configuration can allow for greater variation in total longitudinal length of the catheter 20. Also, as shown, the proximal ends of the first and second cannula portions include radially extending lips that prevent separation of the cannula portions from each and from the hub when the cannula portions are fully extended. Though other gauge sizes are possible, in the present embodiment the first cannula portion 44A is a 15 gauge size while the second cannula portion 44B, which fits inside the first cannula portion, is an 18 gauge size. It is appreciated that one, two, or more telescoping portions can be employed.

Figure 5A:
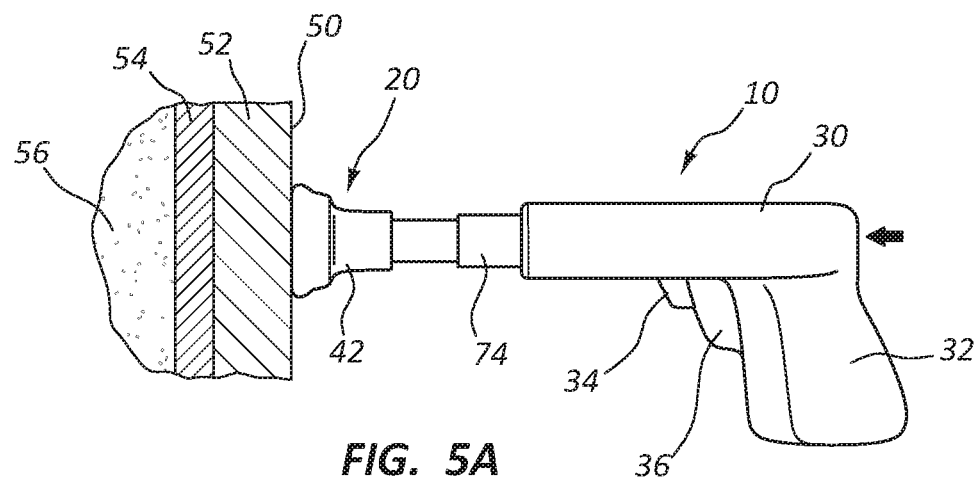
FIGS. 5A-5D depict various stages of use of an access device according to one embodiment.
Figure 5B:
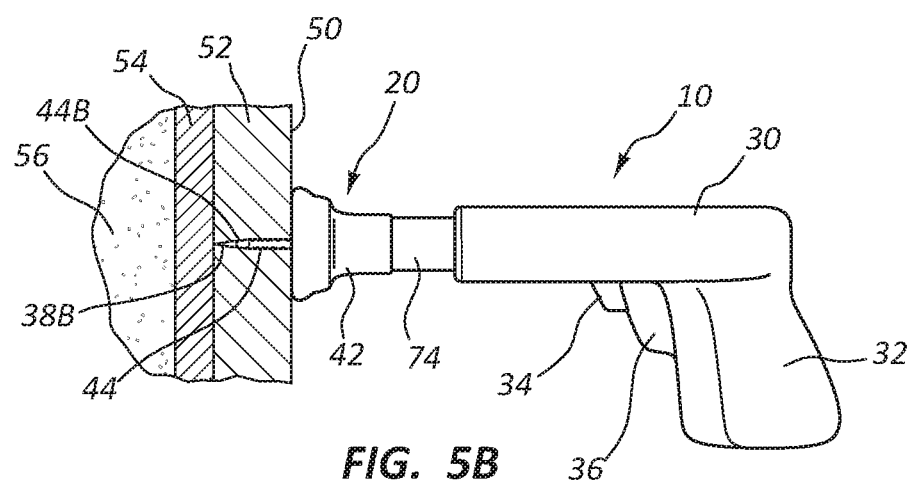

FIGS. 5A depict various features and operation of the access device 10 according to one embodiment, wherein the body 30 includes a telescoping portion that initially shields the trocar 38 prior to access device use. During use of the access device 10, and as shown in FIG. 5A, the user grasps the body 30 of the access device and places the distal end 30B thereof against the skin surface 50. The distal tip 38B of the trocar 38 is then inserted via manual pushing through the skin surface 50 and subcutaneous tissue 52 of the patient until the distal tip of the trocar impacts a wall ("bone wall") 54 of the bone, as shown in FIG. 5B. Note that this action causes the telescoping portion 74 of the access device body 30 to collapse into the more proximal portion of the body so that the trocar 38 can extend from the body. Also, it is appreciated that this action causes the catheter cannula 44, which is disposed about the trocar 38, to be initially retracted at least partially within the catheter hub 42, then extend distally as the trocar extends distally toward the bone wall 54. The configurations of the catheter 20 shown in FIGS. 3A-3D and 4 are examples of suitable catheter configurations that can be utilized with the access device embodiment shown in FIGS. 5A-5D, though other catheter configurations are also possible. As has been discussed, the initial shielding of the trocar 38 by the telescoping portion 74 of the access device body 30 prevents inadvertent contact with the trocar by the user prior to trocar extension from the access device body. In one embodiment, the telescoping portion of the access device body only shields the trocar after use of the access device.

Figure 5C:
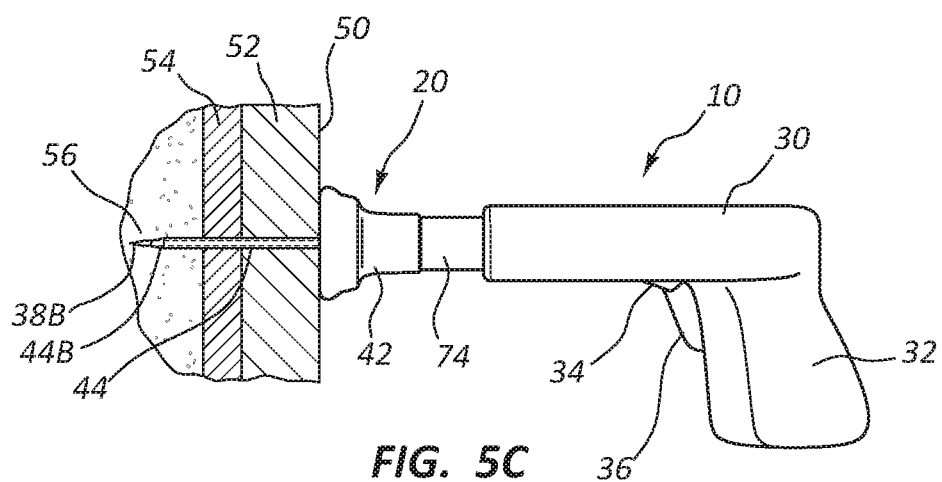

At this point, the safety switch 34 is disengaged by the user and the release trigger 36 is depressed by a finger of the user, which in turn causes the internal spring (or other suitable advancement mechanism) to distally drive the trocar distal tip 38B through the bone wall 54 and into the bone marrow 56 of the bone, as seen in FIG. 5C. This also places the distal tip 44B of the catheter cannula 44 in the bone marrow 56, as desired. Note that, due to the longitudinally extendable nature of the hub 42, the hub rests against the skin surface 50 at the commencement of and throughout the catheter insertion procedure, as seen in FIGS. 5A-5D.

As with the embodiment shown and discussed in connection with FIGS. 2A-2D, the access device 10 and the advancement mechanism are configured to advance the cannula distal tip 44B a predetermined distance into the bone. In this and other embodiments, it is appreciated that the predetermined distance can be varied according to user preference as discussed herein, and that the access device can be configured such that it is capable of advancing the catheter a distance into the bone that is not predetermined before use of the access device.

Figure 5D:
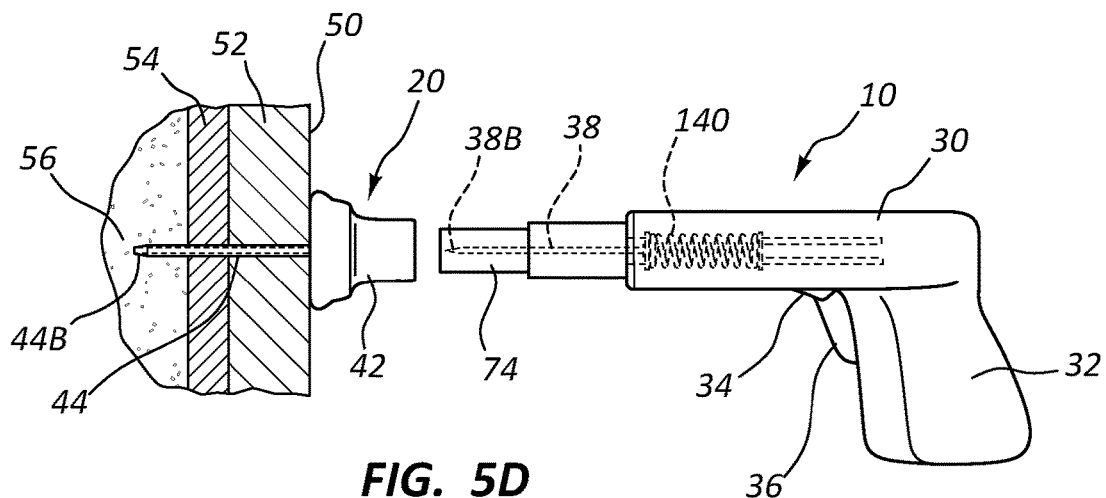

In FIG. 5D, the trocar 38 is withdrawn from the cannula 44 of the catheter 20 by proximally withdrawing the access device body 30, thus causing separation of the access device 10 from the catheter 20. As the access device body 30 is proximally withdrawn, the telescoping portion 74 distally extends to fully cover and shield the trocar 38 upon its removal from the catheter 20, thus preventing an inadvertent needle stick to the user. In one embodiment, interfering surfaces can be included on both the telescoping portion 74 and the catheter 20 to assist in the distal extension of the telescoping portion as seen in FIG. 5D. In another embodiment, the telescoping portion 74 can be manually extended by the user.

After withdrawal of the access device 10, the cannula 44 remains in place with its distal tip 44B disposed within the bone marrow 56, as shown. Note that the catheter hub 42 remains in place against the skin surface 50, as desired. The catheter 20 can be dressed, connected to the extension set 60, and otherwise made ready for infusion of fluids into the bone marrow 56 via the catheter cannula 44.

Figure 6:
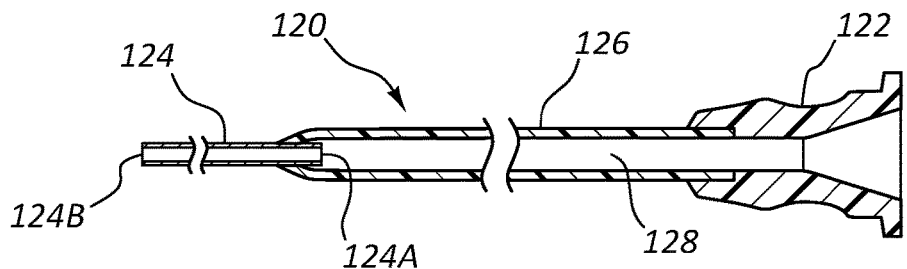
FIG. 6 is a cross-sectional side view of an intraosseous catheter according to one embodiment.
Figure 7:
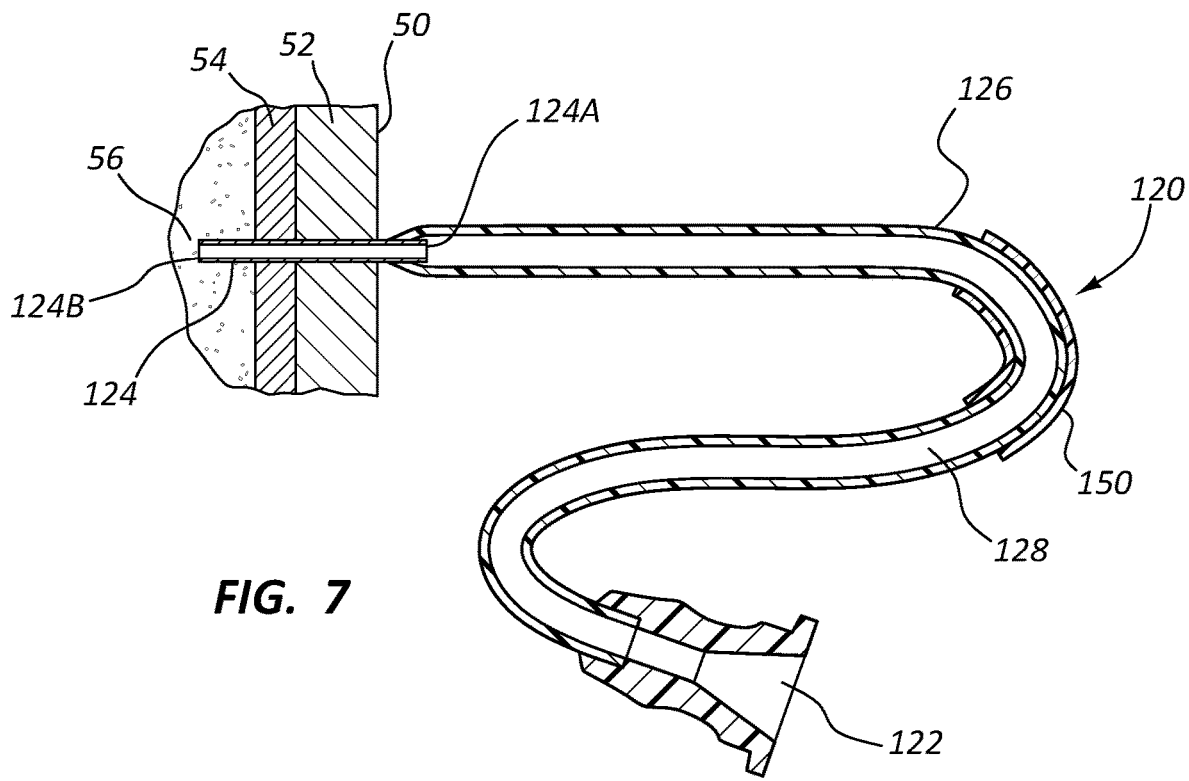
FIG. 7 is a cross sectional side view showing placement of the catheter of FIG. 6.
Figure 8:
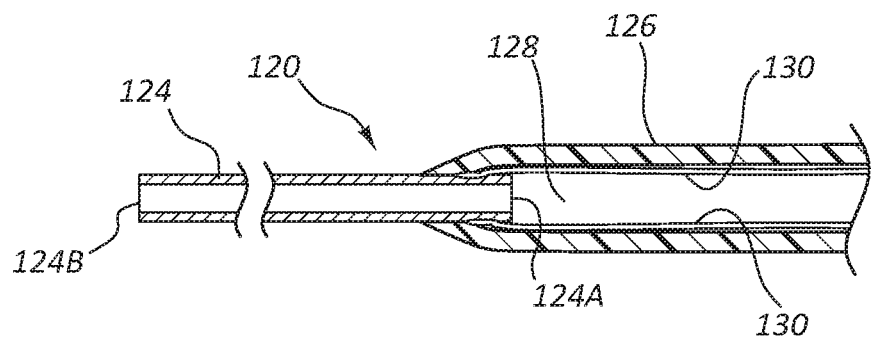
FIG. 8 is a cross-sectional side view of a portion of the catheter of FIG. 6.

FIGS. 6-8 depict details of an example of a catheter 120 that can be employed with the access device 10 according to one embodiment. As shown, the catheter 120 includes on a proximal end a hub 122 configured to operably connect with an extension set, and on a distal end a rigid cannula portion 124 extending between a proximal end 124A and a distal end 124B. A flexible catheter portion 126 operably connects between the hub 122 and the cannula portion 124 and overlaps the proximal end 124A of the cannula portion in the present embodiment. A lumen 128 that serves as a fluid pathway is defined by the hub 122, cannula portion 124, and the catheter portion 126. The cannula portion 124 includes a sufficiently rigid material to penetrate bone without buckling or collapsing, such as stainless steel, peek, or other suitable material including other metals and thermoplastics. The hub 122 and the catheter portion 126 include suitable thermoplastic or other materials in one embodiment.

FIG. 7 depicts the manner in which the catheter 120 is employed, wherein the cannula portion is shown inserted through the bone wall 54 such that its proximal end 124A resides external to the bone wall and its distal end 124B is disposed in the bone marrow 56. A distal segment of the catheter portion 126 extends between the bone wall 54 and the skin surface 50, while the remainder portion of the catheter resides outside the patient. In the present embodiment, a slidable elbow piece 150 is shown disposed over the catheter tube 126. During use, the elbow piece can be slid along the catheter tube 126 and positioned to help conform the catheter tube to the skin surface 50 at the point of exit from the patient body. The elbow piece can include a 90 degree other angle bend to assist with such conformation of the catheter tube 126.

Also note that, though FIG. 7 shows it extending out through the skin surface 50, the cannula portion 124 in one embodiment can be disposed completely internal to the patient body such that a distal portion of the catheter tube 126 is also disposed beneath the skin surface.

FIG. 8 shows that, in the present embodiment, securement wires 130 attached to the proximal end 124A of the cannula portion 124 extend proximally through the lumen 128 of the catheter portion 126 to the hub 122 where they are secured. The securement wires 130 provide necessary strength to enable the cannula portion 124 to be pulled from the bone wall 54 without separating from the rest of the catheter 120. Note that in one embodiment the securement wires 130 can be integrated into the wall of the catheter portion 126. In another embodiment, one, two, or more securement wires 130 can be included. In yet another embodiment, the securement wires 130 extend out past the proximal end of the hub 122. In another embodiment, the securement wires can take other forms, such as a securement ribbons, for instance. These and other variations are therefore contemplated.

Figure 9A:
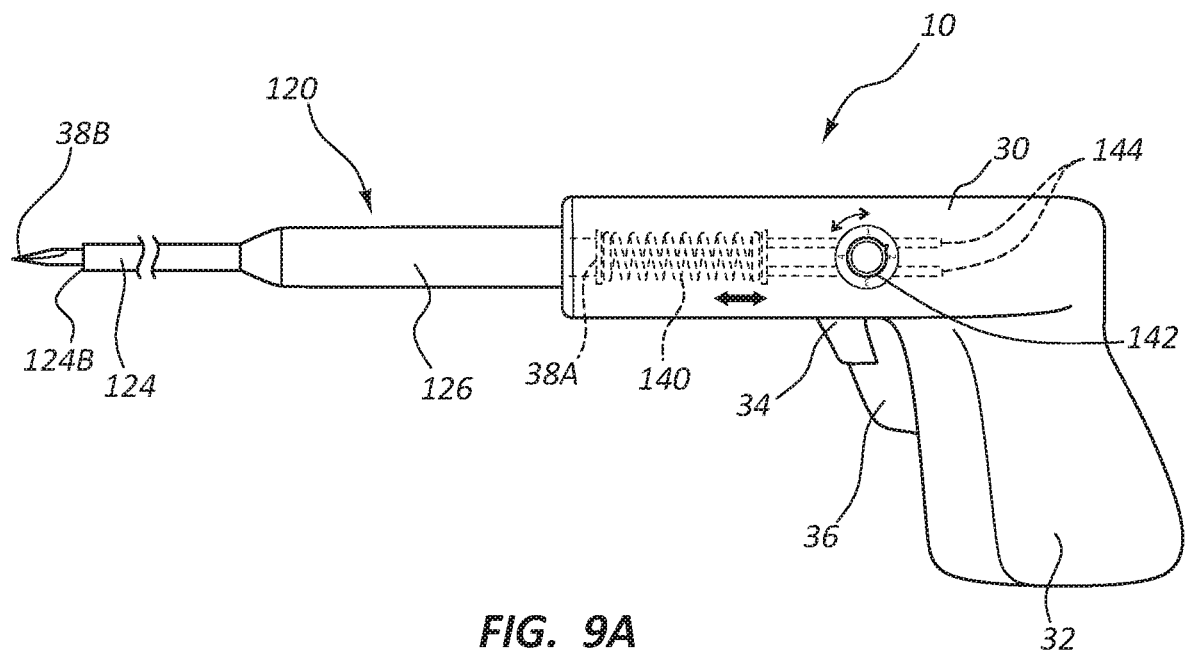
FIGS. 9A and 9B depict various views of the catheter of FIG. 6 and an access device used therewith.
Figure 9B:
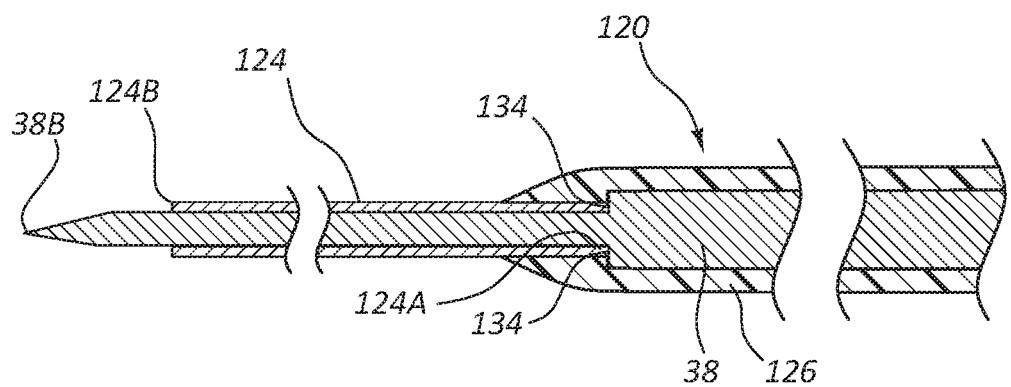

FIG. 9A shows that manner in which the catheter 120 is loaded on the trocar 38 of the access device 10. FIG. 9B shows that the trocar 38 in one embodiment can include a shoulder 134 against which the proximal end 124A abuts when the catheter 120 is disposed on the trocar. This provides the trocar 38 a surface against which to push to advance the catheter 124 through the bone wall 54 and into the bone marrow 56 during use of the access device 30 while still enabling the trocar to readily withdraw from the catheter after catheter placement is complete. Note that the particular location, size, and other configuration of the shoulder can vary from what is shown and described herein.

FIG. 9A further depicts details of an adjustment component configured to adjust the depth to which the advancement mechanism advances the distal tip 38B of the trocar 38 and the catheter 120 (Note that the present discussion regarding the adjustment component can be applied to other embodiments herein). As shown, a spring 140 is included within the access device body 30 and configured as an advancement mechanism to provide a distal advancement force as with other embodiments herein) to the trocar 38 via its proximal end 38A. An adjustment component, here embodied as a rotary adjustment dial 142, is disposed on the surface of the access device body 30 and is movable by a user of the access device to select a predetermined depth to which the distal tip 38B of the trocar 38, and correspondingly, the distal tip 124B of the catheter 120, will be advanced by the spring 140. In the present embodiment, the adjustment dial 142 is operably connected to one or more control arms 144 that are configured to vary the pre-actuation length of the spring 140. This in turn lessens or increases the potential energy stored in the spring 140 prior to actuation, thus providing for relatively more shallow or deep advancement of the trocar 38 and catheter 120 into the bone. In addition to this, other adjustment components and advancement mechanisms can be employed, in other embodiment.

In light of the above, it is appreciated that the spring 140 serves as one example of a selective means for advancing the trocar and the catheter. Note that the spring 140 is considered selective as it is actuated selectively by the user via a trigger or other suitable component. It is appreciated that other structures and components can be employed to provide the same functionality, in other embodiments.

Figure 10:
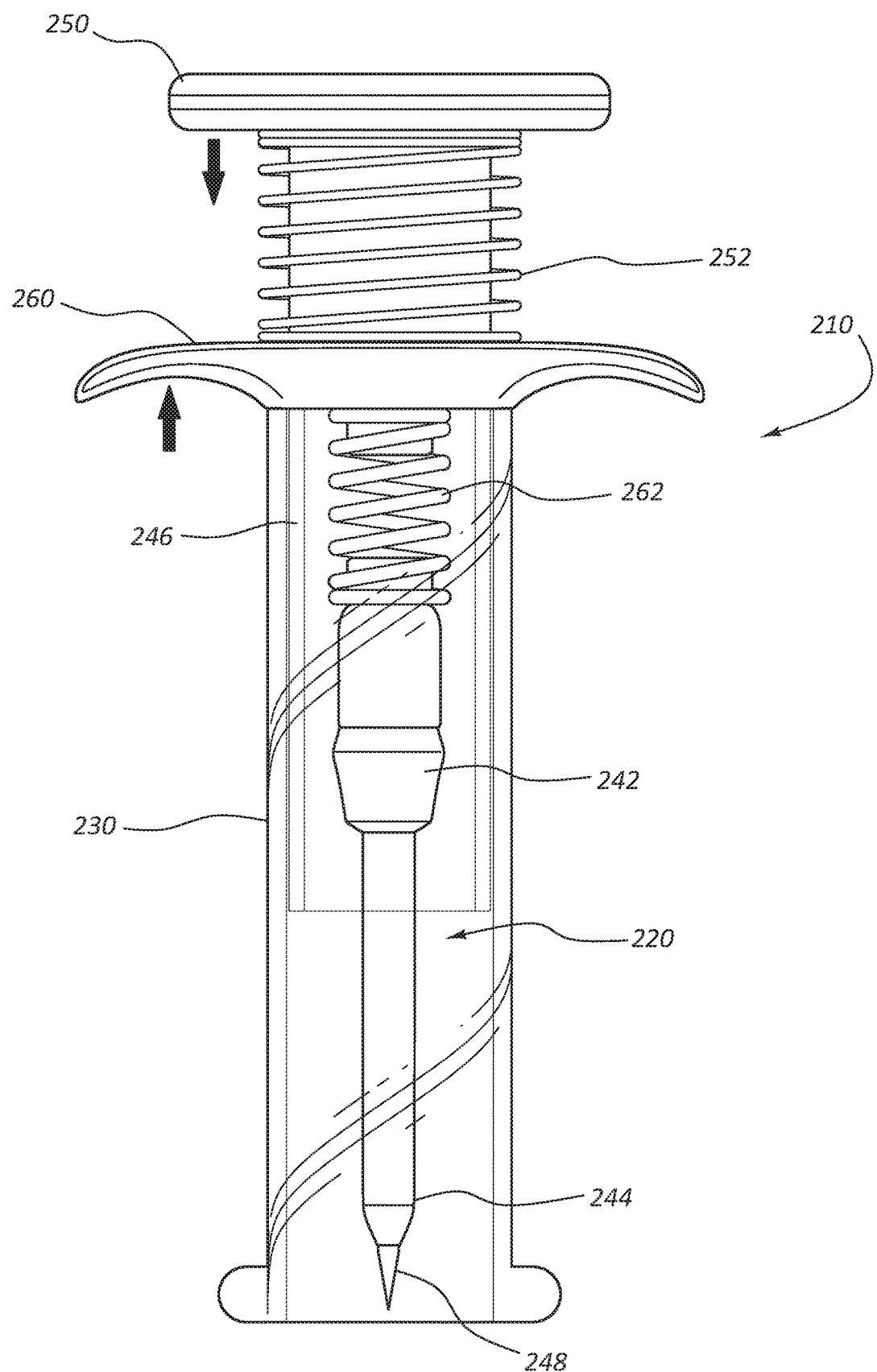
FIG. 10 is a cross-sectional side view of an intraosseous access device according to one embodiment.

FIG. 10 depicts details of an intraosseous access device ("access device") 210 according to one embodiment, including an elongate body 230 inside of which is disposed an intraosseous catheter ("catheter") 220, also referred to as an intraosseous cannula. As before, the catheter 220 includes a hub 242 from which distally extends a cannula 244. The catheter 220 in the present embodiment is slidably disposed over a trocar needle ("trocar") 248 and received within a cartridge 246 that itself is disposed within the access device body 230, as shown.

The access device 210 further includes an advancement mechanism configured to selectively advance the trocar 248 and catheter 220 included therewith in a distal direction during use of the access device 210. In the present embodiment, the advancement mechanism includes a first actuator, here implemented as a first trigger 250 configured to selectively activate a first spring 252, and a second actuator, here implemented as a second trigger 260 configured to selectively actuate a second spring 262. The first spring 252 is a relatively low-force spring configured to provide, when actuated by the first trigger 250 (e.g., by manually depressing the first trigger in a distal direction), a force to distally advance the catheter-containing cartridge 246 out a distal end of the access device body 230 a predetermined distance. This action is employed during use of the access device 210 to advance the trocar 248 and catheter 220 through the skin surface and tissue of the patient to the bone wall. Note that in the present embodiment, the distal end of the cartridge 246 rests against the skin surface after actuation of the first trigger 250 to distal advance the catheter 220.

In contrast, the second spring 262 is a relatively high-force spring configured to provide, when actuated by the second trigger 260 (e.g., by manually pulling the second trigger in a proximal direction), a force to distally advance the catheter 220 from the open distal end of the cartridge 246 a further predetermined distance. This action is employed during use of the access device 210 to advance the distal ends of the trocar 248 and the catheter 220 through the bone wall and into the bone marrow of the patient. The use of the relatively high-force spring 262 is necessary to enable the trocar 248 and catheter 220 to penetrate the relatively stiff and rigid bone wall. Once the distal end of the catheter 220 is in place in the bone marrow of the patient, the trocar can be withdrawn from the patient body by proximally withdrawing the access device body 230 by the user.

It is appreciated that the second spring 262 serves as an example of selective means for advancing the trocar 248 and the catheter 220, and is thus configured to apply the necessary amount of force to cause the above-described penetration of the patient bone wall. The second spring 262 is considered selective as it is actuated by a user via a trigger or other suitable component. It is appreciated that other structures and components can be employed to provide the same functionality, in other embodiments. Note that the first and second springs 252, 262 can be configured to cause penetration of the trocar 248/catheter 220 to different predetermined distances into the bone. In one embodiment, the access device is configured such that the first and second springs cause penetration to a single predetermined depth for each spring. In another embodiment, the access device includes the ability to adjust the force of one or more of the springs to vary the amount of trocar/catheter penetration. These and other modifications are therefore contemplated.

Figure 11:
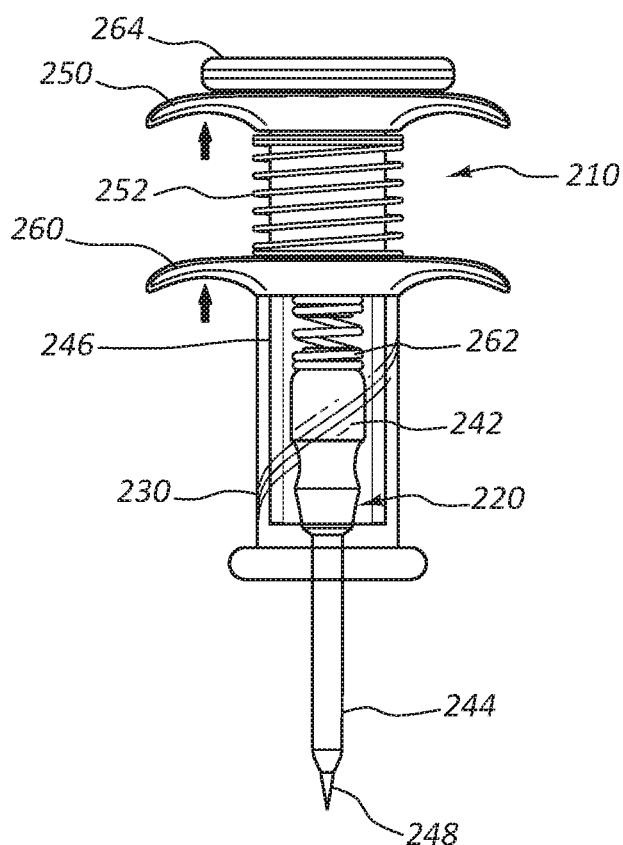
FIG. 11 is a cross sectional side view of an intraosseous access device according to one embodiment.

FIG. 11 depicts the access device 210 according to another embodiment, wherein both the first trigger 250 and the second trigger 260 are configured as triggers to be manually pulled in the proximal direction to actuate the first spring 252 and the second spring 262, respectively. Note that FIG. 11 shows the configuration of the access device 210 after actuation of the first spring 252 by manual proximal pulling of the first trigger 250, wherein the catheter 220 is partially extended from an open distal end of the access device body 230, but before actuation of the second spring 262 by manual proximal pulling of the second trigger 260, which causes further distal ejection of the catheter. In one embodiment, it is appreciated that the access device can be configured such that actuation of the first spring, second spring, or both springs can be performed automatically. Also, in one embodiment, the relatively strong second spring can be sized to fit within (such as concentrically, for instance) the relatively weaker first spring. In another embodiment, the first spring is sized to be received within the second spring.

Figure 12:
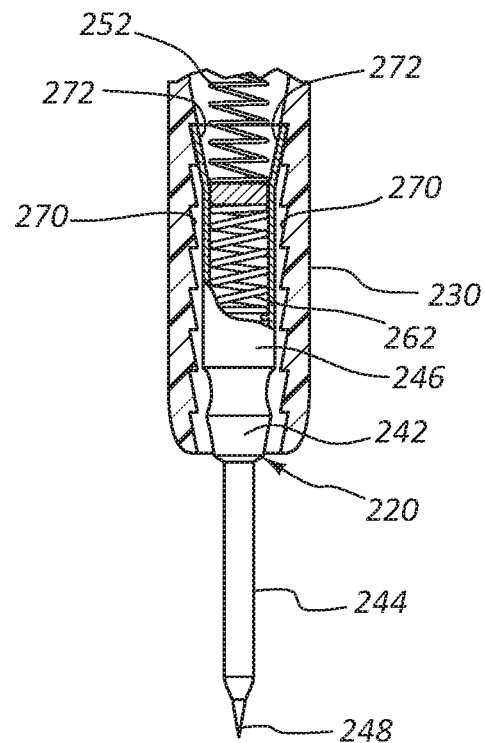
FIG. 12 is a cross-sectional side view of a intraosseous access device according to one embodiment.

FIG. 12 depicts details of an advancement mechanism according to another embodiment, wherein the access device body 230 defines on an inner surface thereof a plurality of ratchet teeth 270 that are configured to engage with two radially extending engagement arms 272 that are included on a proximal portion of the cartridge 246 holding the catheter 220. This arrangement enables the cartridge 246 and included catheter 220 to distally advance in a step-wise fashion without having the ability to withdraw back into the access device body 230. Note that the ratchet components can vary in shape, size, position, and other configuration from what is shown and described herein.

Figure 13:
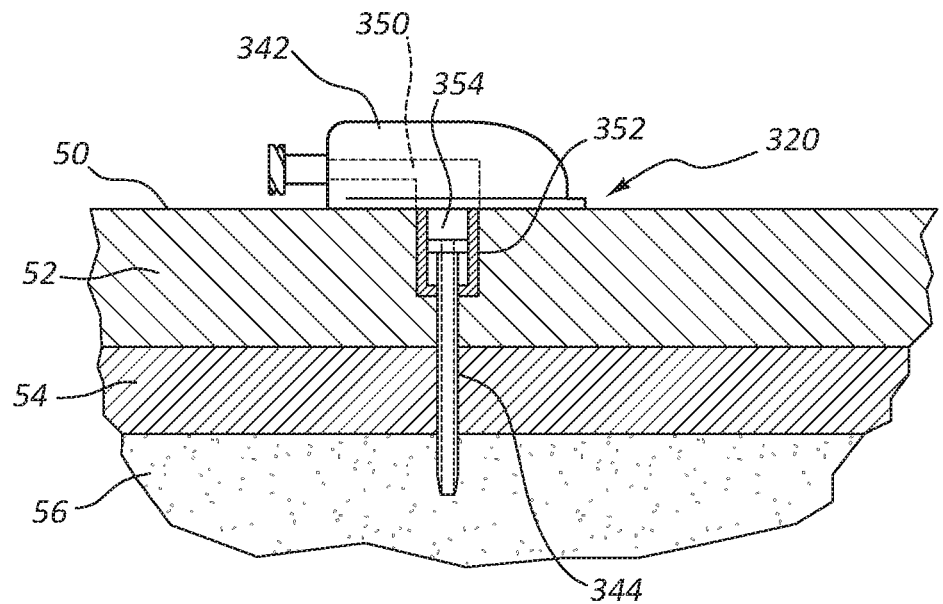
FIG. 13 is a cross-sectional side view of an intraosseous catheter according to one embodiment.
Figure 14:
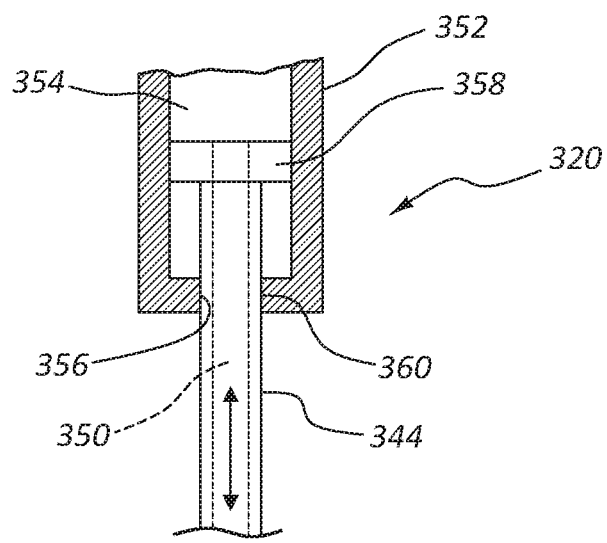
FIG. 14 is a cross-sectional side view of a portion of the catheter of FIG. 13.

FIGS. 13 and 14 depict details of an intraosseous catheter 320 according to one embodiment, including a hub 342 and an elongate cannula 344 distally extending therefrom. The catheter 320 is shown in FIG. 13 in place within a patient, with a distal tip of the cannula 344 extending to the bone marrow 56. A lumen 350 is defined by the catheter 320 to enable infusion of medicaments or other fluids to the bone marrow 56.

FIG. 14 shows that the catheter 320 is adjustable in total length. In light of this, in the present embodiment the hub 342 includes a slide tube defining a cavity 354 and an opening 356 to the cavity. Correspondingly, the cannula 344 is received through the opening 356 and includes on its proximal end a radially extending rim 358 configured to slide proximally/distally within the cavity 354, thus enabling the total longitudinal length to vary according to the position of the rim within the cavity. A seal 360 is placed about the opening 356 to ensure a fluid tight seal between the cannula and the opening. In this way, the catheter 320 can vary in desired length according to bone depth and user preference. If desired, the hub 342 can be adhered to the skin surface 50 after adjustment of the catheter 320 is made to enable the hub to rest against the skin surface.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

What is claimed is:

1. An intraosseous access device, comprising:
   a device body;
   a trocar needle coupled to the device body, the trocar needle including a distal tip designed for insertion into a bone;
   an intraosseous catheter removably disposed on the trocar needle, the intraosseous catheter comprising:
      a hub having a proximal connector portion and a distal base portion;
      a lumen extending through the hub from a proximal end of the proximal connector portion through a distal end of the distal base portion;
      a cannula slidably disposed in the lumen independent of the trocar needle to provide an adjustable cannula length extending from the distal base portion; and
      an O-ring surrounding the cannula in the lumen; and
   an advancement mechanism configured to selectively and distally advance the trocar needle and the cannula into the bone.

2. The intraosseous access device as defined in claim 1, wherein the device body includes a pistol grip shape.

3. The intraosseous access device as defined in claim 1, wherein the advancement mechanism provides a distal advancement force to distally advance the trocar needle and the cannula.

4. The intraosseous access device as defined in claim 3, wherein the advancement mechanism includes a spring, the spring providing the distal advancement force.

5. The intraosseous access device as defined in claim 3, wherein the distal advancement force is variable in magnitude by a user of the intraosseous access device.

6. The intraosseous access device as defined in claim 5, wherein the distal advancement force is user-variable via an adjustment component.

7. The intraosseous access device as defined in claim 6, wherein the adjustment component includes an adjustment dial mounted on the body of the intraosseous access device.

8. The intraosseous access device as defined in claim 7, wherein the advancement mechanism includes a spring and wherein the adjustment component is configured to alter an operable length of the spring prior to distal advancement of the trocar needle and the cannula.

9. The intraosseous access device as defined in claim 1, wherein the advancement mechanism is configured to distally advance the trocar needle and the cannula a predetermined depth into an internal portion of the bone.

10. The intraosseous access device as defined in claim 9, wherein the predetermined depth is adjustable via an adjustment component.

11. The intraosseous access device as defined in claim 1, wherein the advancement mechanism is configured to be actuated by a release trigger.

12. The intraosseous access device as defined in claim 11, wherein the intraosseous access device further includes a safety switch, the safety switch configured to prevent inadvertent actuation of the release trigger.

13. The intraosseous access device as defined in claim 1, wherein the advancement mechanism is configured to distally advance a distal tip of the cannula into an intraosseous portion of the bone.

14. The intraosseous access device as defined in claim 1, wherein the intraosseous access device is configured for placement of the cannula within at least one of a tibia, a sternum, and a humerus bone.

15. The intraosseous access device as defined in claim 1, wherein the trocar needle extends distally from the device body prior to use of the intraosseous access device.

16. The intraosseous access device as defined in claim 1, wherein the advancement mechanism includes at least one of a drill, a chemical-based charge, and a spring.

17. The intraosseous access device as defined in claim 1, wherein the advancement mechanism is disposed within the intraosseous device body.

18. The intraosseous access device as defined in claim 1, wherein the intraosseous device body includes a telescoping portion that is configured to cover the trocar needle prior to use of the intraosseous access device.

19. The intraosseous access device as defined in claim 18, wherein the telescoping portion is configured to cover the trocar needle after the cannula has been inserted into the bone and the trocar needle has been removed from the bone.

* * * * *